United States Patent [19]

Girvan

[11] Patent Number: 5,131,938
[45] Date of Patent: Jul. 21, 1992

[54] BORATE ALGAECIDE AND FUNGICIDE

[76] Inventor: John W. Girvan, 8295-6 Western Way Cir., Jacksonville, Fla. 32216

[21] Appl. No.: 759,851

[22] Filed: Sep. 16, 1991

Related U.S. Application Data

[60] Continuation of Ser. No. 289,498, Dec. 23, 1988, abandoned, which is a continuation of Ser. No. 870,002, Jun. 3, 1986, abandoned, which is a division of Ser. No. 583,014, Feb. 23, 1984, Pat. No. 4,594,091.

[51] Int. Cl.$^5$ .................. A01N 33/14; A01N 59/14
[52] U.S. Cl. .................................. 71/67; 71/128
[58] Field of Search ........................... 71/67, 128

[56] References Cited

U.S. PATENT DOCUMENTS

| | | | |
|---|---|---|---|
| 3,560,381 | 2/1971 | Winters et al. | 7/128 |
| 4,014,676 | 3/1977 | Carter et al. | 71/67 |
| 4,119,535 | 10/1978 | White et al. | 71/67 |
| 4,172,094 | 10/1979 | Dybas et al. | 71/67 |

OTHER PUBLICATIONS

Mabroeuk et al., "Control of Growth and Aflatoxin Production of *Aspergillus flavus* by Some Additives", Chem Abs., vol. 97, 1982.
Merck Index, Tenth Edition, pp. 1323 and 8424 (1983).
Micchiarolo et al., Chem. Abst. vol. 96, 148926j (1982).
Spitiere-Goudeli, et al., "In vitro sensitivity of Canadida to antiseptic agents", Chem Abstracts, vol. 98, 1983.
The Merck Index (1983) p. 184: entry 1320 and p. 1231, entry 8421.

*Primary Examiner*—Marianne M. Cintins
*Assistant Examiner*—John Peabody
*Attorney, Agent, or Firm*—Jones, Askew & Lunsford

[57] ABSTRACT

An algaecide and fungicide containing boron derivatives which are added to standing water systems such as swimming pools, drinking water resevoirs and cooling towers. The boron derivative algaecide and fungicide is effective in killing and repressing unwanted algal and fungal growth.

6 Claims, No Drawings

BORATE ALGAECIDE AND FUNGICIDE

CROSS-REFERENCE TO RELATED APPLICATION

This is a continuation of application Ser. No. 289,498, filed Dec. 23, 1988, now abandoned, which is a continuation of application Ser. No. 870,002, filed June 3, 1986, now abandoned which is a division of application Ser. No. 583,014 filed Feb. 23, 1984 now U.S. Pat. No. 4,594,091.

TECHNICAL FIELD

The present invention relates generally to the field of antimicrobial agents and more particularly relates to a method of killing and repressing algae and fungus growth in standing water such as swimming pools and drinking water reservoirs and cooling towers.

BACKGROUND OF THE INVENTION

Water is a primary transmission vector for the spread of potentially dangerous microorganisms. It is also an excellent growth medium for certain kinds of molds and algae causing unwanted discoloration and turbidity in the water. Some of the organisms that will grow in standing water include Chlorococcum, Chlorella, Cledaphora, Microcystis, Osciliatoris, Spirogyra, Ulaothrix, Vanetteria and the fungus *Aspergillus flavus*. Thus, the prevention or inhibition of growth of potentially harmful microorganisms in water has been a longstanding problem. This is especially true where there is extensive human contact with the water as in bathing or in recreational areas such as swimming pools.

The most common prior art method of water treatment for microorganisms has been to treat the water with halogens such as chlorine. One way of doing this is to inject elemental chlorine directly into the water, usually as the water is being filtered. Although chlorine is an excellent water treatment agent, it has several inherent problems One of the major problems is that it is difficult to maintain the necessary concentration of chlorine in the water to be effective. Chlorine that is dissolved in water will gradually escape in gaseous form. This loss of soluble chlorine is accelerated in direct sunlight. Thus, when using this conventional water treatment method, it is necessary to continuously replace the lost chlorine. Another disadvantage of using elemental chlorine is that it forms hydrochloric acid as it dissolves in the water. This causes a drop in the pH of the water and makes acid-base balancing difficult. Thus, when using chlorine as a water treatment agent, it is also necessary to add a buffer system to the water in order to maintain the proper pH.

Chlorine may also be added directly to water as a powder as a hypochlorite such as sodium hypochlorite. When hypochlorites are dissolved in water, an equilibrium is set up between free chlorine and hypochlorous acid. The active ingredient is the elemental chlorine that is liberated in the equilibrium reaction and is therefore subject to the same problems as outlined above for free elemental chlorine.

Another method of controlling water-borne microorganisms is through the use of halogen substituted organics such as trichloro-S-triazinetrione and bromochlorodimethylhydantoin. This class of water treatment agents do not dissipate as rapidly as elemental chlorine and are much easier to handle and to store. However, they are quite expensive and a buffering system is still required to maintain a proper pH.

SUMMARY OF THE INVENTION

The present invention comprises the use of boron derivatives including boric acid, sodium borates, potassium borates or salts of boron hereafter referred to as borax and is designed to inhibit algal and fungal growth in water. It is especially effective in controlling algal growth in swimming pools and in moist areas such as shower stalls.

The present invention is an advantage over the prior art in that one application of the borate will prevent the growth of unwanted algae and molds over a relatively long period of time when compared to conventional water treatment agents such as chlorine. The present invention is much more economical than the prior art and is easier to use. For example, in swimming pools, the present invention may be administered as a water solution either by injection into the system's filter system or manual addition directly to the water. The borates may also be added directly to the water as a liquid, a powder form or a solid form.

In addition to the unexpected algaecidal and fungicidal activity of the borate derivatives, the compound is an excellent pH buffer when added as boric acid and the borate salt. For example, if the boron derivative is added as 1 part sodium tetraborate pentahydrate to 4 parts boric acid, the resulting solution will be buffered at about pH of 7. Thus, when using the present invention as an algaecidal agent in a swimming pool there is no need to add a buffer system such as a carbonic acid-carbonate buffer. In addition, the boron derivaties cause minimum calcium precipitation, a major problem in a carbonic acid-carbonate water treatment system. The boron treatment embodied in the present invention has also been found, in addition to its algaecidal activity, to enhance the blue color of swimming pools.

Thus it is a primary object of the present invention to provide a system for the prevention of growth of algae and molds in water.

It is a further object of the present invention to provide a system for the economical control of algae and mold growth in swimming pools.

It is a further object of the present invention to provide an economical buffer system for maintaining the pH of the treated water.

It is still a further object of the present invention to provide an algaecidal system for winterizing swimming pools.

It is a further object of the present invention to provide a water purification system for drinking water.

It is a further object of the present invention to provide a colorizing agent for swimming pools.

It is a further object of the present invention to provide a system for the control of algae in wet areas such as shower stalls.

These and other objects, features and advantages will become apparent from a review of the following detailed description of the invention and the appended drawings and claims.

DETAILED DESCRIPTION OF THE PRESENT INVENTION

The algaecidal activity of the boron derivatives was tested using standard pure culture techniques published by the Environmental Protection Agency TSD designation 6.101. The following testing procedure was used in all examples.

The standard test organisms are Chlorella pyrenoidosa, and Chlorococcum mustard. Algae cultures are available from a Culture Collection of Algae, Department of Botany, Indiana University, Bloomington, Indiana. The algae culture is prepared by adding 30 ml of sterile Allen's medium (see Allen, M.B., *The Cultivation of Myxophyceae*, Arch. Mikrobiol., 17:34–53 (1952) to a 50 ml Erlenmeyer flask. A stock cell suspension (0.01 ml) is transferred to the flask and is incubated at 22 to 24 C under 16 hours of fluorescent light for up to four weeks time. This suspension is used in all tests using C. pyrenoidosa. Other species of algae used in testing were appropriately identified.

The algaecidal test was performed by placing 30 ml of Allen's medium into a 50 ml Erlenmeyer flask using a Brewer Automatic Pipetting Machine. The flasks were then plugged with cotton and sterilized by autoclaving at 121 degrees centigrade for 20 minutes. When cooled the flasks were inoculated with *C. pyrenoidosa* (or other organism) at a concentration which resulted in an initial organism concentration of approximately 300,000 cells/ml. All tests were performed with six identical samples.

Cells were counted using a Spencer Bright Line Hemacytometer. To determine the algaecidal properties of the borate, 0.01 ml aliquots of the stock organism were aseptically transferred from the original treated flasks after two days to six additional 50 ml Erlenmeyer flasks containing 30 ml of sterile Allen's medium. The cultures were incubated in a controlled environment chamber under conditions previously described for three weeks. The number of cells was tested at the beginning of the experiment and at the end of each week. The amount of algae growth in the test flasks was qualitatively rated as follows.

0 = no visible growth
1 = very slight growth
2 = slight growth
3 = moderate growth
4 = heavy growth
5 = very heavy growth For a product to be considered to have a satisfactory algaestatic activity, it must provide at least 70% control of growth for three weeks in the original six flasks. Percent control is obtained by subtracting average rating figure of treated flasks (Rt) from average rating figure of untreated flasks (Rc), then dividing by the average rating figure of the untreated flasks (Rc), multiplied by 100.

$$\text{Percent control} = \frac{100(Rc - Rt)}{Rc}$$

Algaecidal activity is defined as no indication of growth in subcultures after three weeks.

EXAMPLE 1

A dose-response curve was performed using Chlorococcum as the test organism. The test was performed as described above using a control and six different concentrations of sodium tetraborate pentahydrate (hereinafter borate) in place of the normal phosphate buffer of Allen's medium. The amount of algae growth in the test flasks was rated as previously described.

TABLE 1

|  | Control | Borate - mg/l | | | | | |
|---|---|---|---|---|---|---|---|
|  |  | 12.5 | 5 | 25 | 50 | 100 | 200 | 400 |
| 1st week | 1 | 1 | 1 | 0 | 0 | 0 | 0 | 0 |
| 2nd week | 5 | 3 | 2 | 0 | 0 | 0 | 0 | 0 |
| 3rd week | 5 | 5 | 5 | 0 | 0 | 0 | 0 | 0 |

As shown, a single addition of borate at a concentration of 25 mg/l or greater completely inhibited any Chlorococcum growth.

EXAMPLE 2

The effect of borate on the growth of the algae chlorococcum mustard and Chlorella pyrenoidosa and on the mold Aspergillus is shown in this example. The tests were performed as described above. The borate concentration was 200 mg/l for all tests.

TABLE 2

|  | Control | Organism | | |
|---|---|---|---|---|
|  |  | Chlorococcum | Chlorella | Aspergillus |
| 1st week | 1 | 0 | 0 | 0 |
| 2nd week | 4 | 0 | 0 | 0 |
| 3rd week | 5 | 0 | 0 | 0 |

EXAMPLE 3

In this example, the latent effect of inculation of the organism in borate is measured. The test organism was incubated in the indicated borate solution for 48 hours and then washed by centrifugation. The organisms were then resuspended in fresh Allen's medium without borate and tested weekly for microbicidal and microstatic activity.

Microbicidal activity was measured as follows
A = average cell count of control organisms
B = average cell count of the treated organisms.

$$\text{Percent Control} = 100 \frac{(A - B)}{A}$$

Microstatic activity was measured as follows:
A = average cell count of control organisms
B = average cell count of the treated organisms.

$$\text{Percent Control} = 100 \frac{(A - B)}{A}$$

Using the above formulas for calculating the efficiency of the algaecidal activity, the effect of different concentrations of borate on Chlorococcum species is shown in the following table. Experimental conditions are identical to those described previously.

TABLE 3

| Borate in mg/l | 12.5 | 25 | 50 | 100 | 200 | 400 |
|---|---|---|---|---|---|---|
| Static 1st week | 72.7 | 81.8 | 100 | 100 | 100 | 100 |
| Cidal | 93.6 | 93.6 | 15.3 | 96.6 | 97.3 | 97.3 |
| Static 1st week | 81.8 | 90.9 | 100 | 100 | 100 | 100 |
| Cidal | 74.2 | 74.2 | 89.2 | 90.5 | 93.2 | 93.2 |
| Static 1st week | 63.6 | 72.7 | 90.9 | 100 | 100 | 100 |
| Cidal | 0 | 50.4 | 72.8 | 90.4 | 88.0 | 92.0 |

As demonstrated in the above table, a 48 hour exposure of Chlorococcum species to borate concentrations greater than 50 mg/l showed significant algaestatic activity while borate concentrations greater than 100 mg/l showed significant algaecidal activity even after three weeks.

EXAMPLE 4

The effect of a 48 hour exposure to 200 mg/l of borate on several different species of algae and mold is shown in the following table. The organisms used in this example were Chlorococcum species, *Chlorella pyrenoidosa* and *Aspergillus flavus*. The first two organisms are algae and the third is a common mold. The same calculations are performed as in Example 4.

TABLE 4

|  | Organism | | |
|---|---|---|---|
|  | Chlorococcum | Chlorella | Aspergillus |
| Static 1st week | 100 | 100 | 100 |
| Cidal | 89.1 | 92.8 | 96.1 |
| Static 1st week | 100 | 100 | 100 |
| Cidal | 91.0 | 90.71 | 96.7 |
| Static 1st week | 100 | 100 | 100 |
| Cidal | 90.4 | 90.4 | 96.5 |

As summarized in this table, incubation of the organism in borate concentrations of o200 mg/l for 48 hours is highly effective in controlling and killing the two algae Chlorococcum species and the *Chlorella pyrenoidosa* and the mold Aspergillus flavus.

EXAMPLE 5

Boron derivatives can be used in combination with a sanitizer to treat a water system. Pool sanitizers such as halogens (chlorine or bromine), copper, hydrogen peroxide, ozone, oxone and quaternary ammonium compounds have been used by those by those skilled in the art. The embodiment of the present invention used in this example is sodium or potassium tetraborate pentahydrate (hereinafter borate) in concentrations of about twenty-five mg/liter and bromine (as bromochlorodimethylhydantoin) in concentrations approximating 0.5 to 1.5 mg/liter. The halogen additive is constantly fed into the pool by standard procedures well known in the art. The objective in a water treatment system is to maintain optimal water parameters over a period of time. The optimal parameters for a swimming pool are approximately as follows:
1. pH - No change
2. total alkalinity should be held at approximately 200 to 250 ppm
3. Calcium concentration - 300 to 350 ppm.
4. Oxidizer - Bromine (bromochlorodimethylhydantoin) as 0.5 mg/l Total Dissolved Solids (TDS) in the water - 500 to 1000 ppm.

This Example demonstrates the stability of the borate algaecidal system. In this ex ample, a thirty thousand gallon pool was monitored from May of 1982 to September of 1982. The pool was used daily by an average of four bathers for an average of 1 hours per day. A filter cycle of twelve hours per day was used.

TABLE 5

| Test date | pH | Alk ppm | Ca ppm | Solid ppm | FAB mg/l | Borate mg/l | Algae |
|---|---|---|---|---|---|---|---|
| 5/3 | 7.3 | 120 | 200 | 750 |  | 25 | 0 |
| 5/10 | 7.7 | 140 | 200 | 750 | 0.9 | 25 | 0 |
| 5/17 | 7.9 | 150 | 200 |  | 0.7 |  | 0 |

TABLE 5-continued

| Test date | pH | Alk ppm | Ca ppm | Solid ppm | FAB mg/l | Borate mg/l | Algae |
|---|---|---|---|---|---|---|---|
| 5/24 | 8.0 | 160 | 200 |  | 0.5 |  | 0 |
| 6/7 | 8.0 | 165 | 200 | 750 | 0.2 |  | 0 |
| 6/14 | 8.0 | 160 | 200 |  | 0.5 |  | 0 |
| 6/21 | 8.0 | 170 | 200 |  | 0.7 |  | 0 |
| 6/28 | 8.0 | 165 | 200 |  | 0.9 |  | 0 |
| 7/5 | 8.0 | 160 | 200 |  | 0.7 |  | 0 |
| 7/12 | 8.0 | 160 | 200 |  | 0.5 |  | 0 |
| 7/19 | 8.0 | 160 | 200 |  | 0.5 |  | 0 |
| 7/24 | 8.0 | 160 | 200 |  | 0.4 |  | 0 |
| 8/2 | 8.0 | 165 | 200 |  | 3.0 |  | 0 |
| 8/9 | 8.0 | 160 | 200 |  | 0.5 |  | 0 |
| 8/16 | 8.0 | 175 | 200 |  | 0.9 |  | 0 |
| 8/23 | 8.0 | 160 | 200 |  | 0.5 |  | 0 |
| 8/30 | 8.0 | 165 | 200 |  | 0.5 |  | 0 |

EXAMPLE 6

By increasing the borate concentration, the halogen agent can be completely deleted from the water treatment formula. This is shown in the results of the field test in Table 6. In this example, a thirty thousand gallon marblelite pool was monitored from March of 1983 to September of 1983 using only borate as the water treatment agent. The pool was used daily by an average of four bathers for an average of one hour per day. A filter cycle of twelve hours per day was used. The borate (sodium tetraborate pentahydrate) was added to a final concentration of approximately 100 mg/l. Algal growth was measured visually. No algae growth was visually apparent throughout the test period.

TABLE 6

| Test date | pH | Ca ppm | Solid ppm | Borate lbs pounds | Acid HCl | Quant. Ammonia oz. | Algae | Bacterial culture |
|---|---|---|---|---|---|---|---|---|
| 3-22 | 8.4 | 230 | 600 | 5 | 12 | 0 | Neg. |  |
| 3-28 | 7.9 | 240 | 600 | 0 | 0 | 0 | Neg. |  |
| 4-4 | 8.0 | 220 | 650 | 0 | 0 | 0 | Neg. |  |
| 4-11 | 7.7 | 220 | 550 | 0 | 1 | 0 | Neg. |  |
| 4-18 | 8.2 | 250 | 550 | 1 | 0 | 0 | Neg. |  |
| 4-25 | 8.2 | 230 | 600 | 5 | 5 | 0 | Pos. |  |
| 4-27 |  |  |  | 40 | 9.6 | 0 | Neg. |  |
| 4-28 | 8.4 | 248 | 600 | 0 | 0 | 0 | Neg. |  |
| 4-29 |  |  |  | 10 | 0 | 0 | Neg. |  |
| 5-1 | 8.5 | 250 | 700 | 27 | 19.2 | 0 | Pos. | Positive |
| 5-2 |  |  |  | 38 | 0 | 0 | Neg. |  |
| 5-3 |  |  |  | 20 | 9.6 | 0 | Neg. |  |
| 5-4 |  |  |  | 20 | 0 | 0 | Neg. |  |
| 5-5 |  |  |  | 20 | 0 | 0 | Neg. |  |
| 5-9 | 8.6 | 230 | 850 | 3 | 9.6 | 0 | Neg. | Positive |
| 5-16 | 8.5 | 242 | 850 | 0 | 9.6 | 0 | Neg. |  |
| 5-23 | 8.6 | 240 | 800 | 0 | 0 | 0 | Neg. | Negative |
| 5-24 |  |  |  |  | 9.6 | 0 | Neg. |  |
| 5-30 | 8.3 | 240 | 850 | 17 | 9.6 | 0 | Pos. | Positive |
| 6-6 | 8.5 | 206 | 750 | 10 | 9.6 | 0 | Neg. |  |
| 6-9 |  |  |  | 10 | 0 | 0 | Pos. |  |
| 6-13 | 8.4 | 220 | 750 | 0 | 9.6 | 0 | Neg. |  |
| 6-20 | 8.3 | 196 | 800 | 5 | 4.8 | 10 | Pos. | Positive |
| 6-24 |  |  |  | 5 | 4.8 | 10 | Pos. |  |
| 6-27 | 8.3 | 200 | 800 | 5 | 4.8 | 6 | Neg. |  |
| 7-4 | 8.3 | 204 | 800 | 0 | 0 | 6 | Neg. | Negative |
| 7-11 | 8.4 | 200 | 800 | 7 | 0 | 6 | Neg. |  |
| 7-14 | 8.3 |  |  | 0 | 4.8 | 6 | Neg. |  |
| 7-18 | 8.3 | 210 | 800 | 0 | 0 | 6 | Pos. | Positive |
| 7-25 | 8.3 | 220 | 800 | 0 | 0 | 6 | Neg. | Negative |
| 8-1 | 8.3 | 210 | 800 | 0 | 0 | 6 | Neg. | Negative |
| 8-8 | 8.3 | 200 | 800 | 0 | 0 | 6 | Neg. | Positive |
| 8-15 | 8.3 | 210 | 800 | 0 | 0 | 6 | Neg. |  |
| 8-22 |  |  |  | 0 | 0 | 6 | Neg. |  |
| 8-29 | 8.3 | 210 | 800 | 0 | 0 | 6 | Neg. | Negative |
| 9-5 | 8.3 | 200 | 750 | 0 | 0 | 0 | Neg. |  |

As shown in Table 6, the present invention was highly effective even without the addition of a sanitizer. The borate only had to be added as a result of dilution during filling the pool. Maintenance of the proper pH is greatly simplified as a result of the high buffering capacity of the present invention. One can obtain even greater buffering control by adding the borate as a 1 to 2 ratio of sodium tetraborate pentahydrate to boric acid.

EXAMPLE 7

The control of mold and algae in shower stalls may be accomplished by making a saturated solution of sodium tetraborate pentahydrate, then spraying it onto tile and grout surfaces of the stall. The surfaces are then scrubbed with a fiber brush, resprayed with the borate solution and allowed to stand for 30 minutes. The surface is then washed with water. This procedure is repeated approximately once a month.

EXAMPLE 8

The present invention can be used to winterize swimming pools by the following procedure. One week before the pool is to be closed for the winter, the normal closing procedures are followed with the additional step of adding borate to a final concentration of 50 mg/l. thereof, it will be understood that variations and modifications can be effected within the spirit and scope of the invention as described in the appended claims.

I claim:

1. A method for controlling algae growth in water comprising adding to the water an effective amount of bromochlorodimethylhydantoin and an effective amount of a derivative of boron wherein said derivative of boron is selected from the group consisting of sodium tetraborate and potassium tetraborate.

2. The method of claim 1, wherein the derivative of boron is sodium tetraborate.

3. The method of claim 1, wherein the derivative of boron is potassium tetraborate.

4. An algaecidal composition comprising an effective amount of bromochlorodimethylhydantoin and an effective amount of a derivative of boron wherein said derivative of boron is selected from the group consisting of sodium tetraborate and potassium tetraborate.

5. The composition of claim 4, wherein the derivative of boron is sodium tetraborate.

6. The composition of claim 4, wherein the derivative of boron is potassium tetraborate.

* * * * *